United States Patent
Foguet et al.

(10) Patent No.: US 6,187,793 B1
(45) Date of Patent: Feb. 13, 2001

(54) 7-[(PIPERIDIN-1-YL)-PROPOXY]-CHROMEN-4-ONE DERIVATIVES, THEIR PREPARATION AND THEIR PHARMACEUTICAL USE

(75) Inventors: Rafael Foguet; Jordi Bolós; Aurelio Sacristán; Josep M. Castelló; José A. Ortiz, all of Barcelona (ES)

(73) Assignee: Ferrer Internacional, S.A., Barcelona (ES)

( * ) Notice: Under 35 U.S.C. 154(b), the term of this patent shall be extended for 0 days.

(21) Appl. No.: 09/380,092

(22) PCT Filed: Dec. 29, 1998

(86) PCT No.: PCT/EP98/08497

§ 371 Date: Dec. 21, 1999

§ 102(e) Date: Dec. 21, 1999

(87) PCT Pub. No.: WO99/35144

PCT Pub. Date: Jul. 15, 1999

(30) Foreign Application Priority Data

Dec. 30, 1997 (ES) .................................................. 9702718

(51) Int. Cl.[7] ........................ A61K 31/445; C07C 401/14
(52) U.S. Cl. .......................................... 514/321; 546/198
(58) Field of Search .............................. 514/321; 546/198

(56) References Cited

U.S. PATENT DOCUMENTS

| 4,678,787 | * | 7/1987 | Jaen et al. | 514/253 |
| 5,100,902 | * | 3/1992 | Peglion et al. | 514/321 |
| 5,385,916 | * | 1/1995 | Howard | 514/321 |

FOREIGN PATENT DOCUMENTS

| 9632389 | 10/1996 | (WO) . |
| 96/32389 | * 10/1996 | (WO) .................................. 514/321 |

* cited by examiner

Primary Examiner—James H. Reamer
(74) Attorney, Agent, or Firm—Birch, Stewart, Birch & Kolasch LLP

(57) ABSTRACT

7-[3-[4-(6-Fluorobenzo[d]isoxazol-3-yl)piperidin-1-yl]propoxy]-chromen-4-one derivatives having the formula (I):

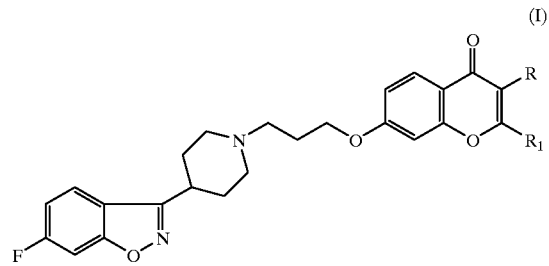

wherein R is hydrogen, CHO, $CH_2OR_2$ or COOH; $R_1$ is hydrogen or $CH_2OH$; and $R_2$ is alkyl having 1 to 4 carbon atoms with the proviso that one of substituents R and $R_1$ should be hydrogen, as well as their pharmaceutically acceptable salts. The process for their preparation and the pharmaceutical compositions containing them are also described. The compounds are new and are useful in the treatment of psychosis, schizophrenia and allergy.

7 Claims, No Drawings

7-[(PIPERIDIN-1-YL)-PROPOXY]-CHROMEN-4-ONE DERIVATIVES, THEIR PREPARATION AND THEIR PHARMACEUTICAL USE

This application is the national phase under 35 U.S.C. §371 of PCT International Application No. PCT/EP98/08497 which has an international filing date of Dec. 29, 1998 which designated the United States of America.

The present invention relates to 7-[3-[4-(6-fluorobenzo[d]isoxazol-3-yl)piperidin-1-yl]propoxy]-chromen-4-one derivatives having the general formula (I):

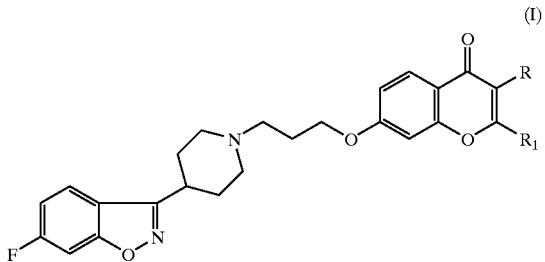

wherein R is hydrogen, CHO, $CH_2OR_2$ or COOH; $R_1$ is hydrogen or $CH_2OH$; and $R_2$ is alkyl having 1 to 4 carbon atoms with the proviso that one of substituents R and $R_1$ should be hydrogen, as well as their pharmaceutically acceptable addition salts.

The compoounds of the present invention are new and are obtained by reacting 2 (or 3)-substituted 7-(3-halopropoxy)-4H-1-benzopyran-4-one of general formula (II), wherein R and $R_1$ is as defined for (I) and X is a halogen selected preferably between chlorine or bromine, with 6-fluoro-3-(4-piperidinyl)-benzo[d]isoxazole (III), according to Scheme 1, in the presence of a base selected between an alkali or earth-alkali metal carbonate or bicarbonate and a catalytic quantity of potassium iodide. The reaction occurs conveniently under heating and in a nonpolar medium, such as that composed of a solvent selected from N,N-dimethylformamide, acetonitrile or the like.

Scheme 1

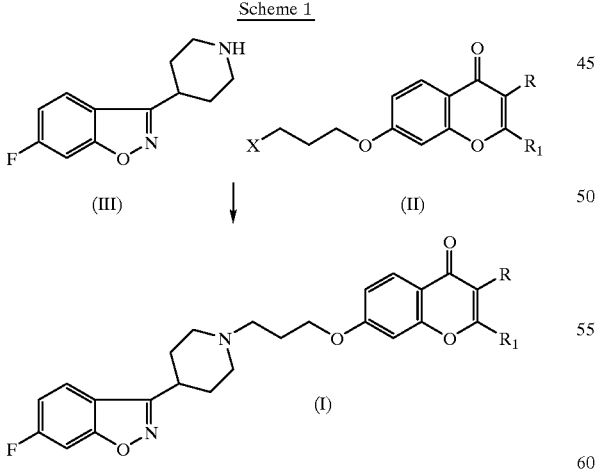

Alternatively, the compounds (I, R:CHO, $R_1$:H) and (I, R:$CH_2OR_2$, $R_1$:H) can also be obtained from 7-[3-[4-(6-fluorobenzo[d]isoxazole-3-yl)piperidin-1-yl]propoxy]-3-(hydroxymethyl)-chromen-4-one (Spanish Patent Application No. 9600323) by oxidation or by alkylation, respectively. The oxidation is conducted conveniently with oxalyl chloride and dimethyl sulfoxide in a halogenated solvent, preferably dichloromethane. The alkylation is conducted conveniently with the corresponding alcohol $R_2$—OH (IV), wherein $R_2$ is as defined for (I), in an acid medium and at the boiling temperature of the mixture. From the new compounds of general formula (I), their salts may be obtained by adding respective acids according to conventional methods of Organic Chemistry.

Spanish Patent Applications No. 9500737 and 9600323 describe chromene derivatives with neuroleptic and anxiolytic action.

The properties of the compounds of the present invention are different from those of the compounds disclosed in the aforesaid patents. In fact, the applicants have found out that the compounds of the general formula (I) exhibit, in addition to a potent action on $D_2$ and 5-HT2A receptors which is of their own as antipsychotic agents, an important action on histamine $H_1$ receptors. In contrast, a $H_1$-antihistamic action has not been previously reported for any of the compounds of the preceding patents.

Specific binding to $D_2$, 5-$HT_{2A}$ and $H_1$ receptors was tested as follows:

$D_2$ receptors: A 2-nM solution of radioactive spiperone ([$^3$H]spiperone), which acts as a specific ligand, was incubated with the membrane corresponding to 20 mg of rat striatum for 20 min at 35° C. buffered at pH 7.4 with Tris.HCl. The non-specific binding was then determined by addition of a micromolar concentration of unlabelled spiperone. $IC_{50}$ (inhibitory concentration 50%) was calculated from the inhibition rate of the specific binding obtained by addition of eleven different concentrations of the compounds to be tested. After the incubation was completed, the sample was filtered through a glass fiber filter and then washed three times with Tris.HCl buffer. The amount of receptor-bound radioactivity was retained on the membrane and determined by liquid scintillation counting.

$5HT_{2A}$ receptors: A 0.5 nM solution of radioactive ketanserin ([$^3$H]ketanserin), which acts as a specific ligand, was incubated with the membrane corresponding to 1 mg of rat cortex for 30 min at 35° C. buffered at pH 7.4 with Tris.HCl. Non-specific binding was then determined by addition of 5 micromolar concentration of unlabelled mianserin. $IC_{50}$ (inhibitory concentration 50%) was calculated from the inhibition rate of the specific binding obtained by addition of eleven different concentrations of the compounds to be tested. After the incubation was completed, the sample was filtered through a glass fiber filter and then washed three times with Tris.HCl buffer. The amount of receptor-bound radioactivity was retained on the membrane and determined by liquid scintillation counting.

$H_1$ receptors: Testing for activity was performed by incubation of guinea-pig cerebellum membranes, in the presence or absence of test compounds, in a 1 nM solution of [$^3$H]-pyrilamine as a specific marker at 25° C. for 60 minutes. The bound radioactivity was separated by filtration (Whatman GF/B) in a Brandel Harvester. The amount of receptor-bound radioactivity present in the filters was determined using a Packard 1800TR counter. The specific binding was established with a 1 µM concentration of triprolidine.

The biochemical results expressed as $IC_{50}$ in molar concentrations are presented comparatively to the compound of Example 2' in Spanish Patent Application No. 9600323 and to standard haloperidol in Table 1 for $D_2$ and $^5$-HT2A receptors, and comparatively to the compound of Example 2' in Spanish Patent Application No. 9600323 and to standard promethazine in Table 2 for $H_1$ receptors.

TABLE 1

| Compound | $D_2$ | $5\text{-HT}_{2A}$ |
|---|---|---|
| Example 1 | $1.31 \times 10^{-8}$ | $2.11 \times 10^{-9}$ |
| Example 2 | $1.28 \times 10^{-8}$ | $5.94 \times 10^{-10}$ |
| Ex. 2' (ES 9600323) | $1.72 \times 10^{-8}$ | $3.08 \times 10^{-9}$ |
| Haloperidol | $1.37 \times 10^{-8}$ | $1.04 \times 10^{-7}$ |

From the data of Table 1 it can be concluded that the compounds of Examples 1 and 2 of the present invention are more potent as ligands of $D_2$ and $5\text{-HT}_{2A}$ receptors than the compound of Example 2' of Spanish Patent Application No. 9600323. The ratio $D_2/5\text{-HT}_{2A}$ shows that all the compounds are superior to standard haloperidol, which results in a lower risk of extrapyramidal effects.

TABLE 2

| Compound | $H_1$ |
|---|---|
| Example 3 | $3.39 \times 10^{-10}$ |
| Example 6 | $1.01 \times 10^{-9}$ |
| Ex. 2' (ES 9600323) | $1.20 \times 10^{-9}$ |
| Promethazine | $8.93 \times 10^{-10}$ |

Similarly, from the data of Table 2 it can be concluded that the compounds of Examples 3 and 6 of the present invention are more potent as ligands of $H_1$ receptors than the compounds of Example 2' in the Spanish Patent Application No. 9600323 and of the same order as promethazine. In addition, the potency of the compound of Example 3 is greater than that of standard promethazine.

The compounds of the present invention were compared with the compound of Example 2' of Spanish Patent Application No. 9600323 in Animal Pharmacology by the inhibition test of apomorphine-induced climbing behaviour (P.Protais et al: "Psychopharmacology", 50, 1–6, 1976). For the practical performance of this experiment, male Swiss mice weighing 22–24 g were used. One week prior to experiment, animals were kept in our facilities at a temperature of 20–22° C. and 12/12 h light-dark cycle, and had free access to food and water. Two hours prior to experiment, the animals were placed in individual cages without access to food.

Animals were administered orally with test drug or 0.25% agar at time 0. After 60 minutes, apomorphine was subcutaneously injected at a dose of 1 mg/kg, and after further 70 minutes the animal's behaviour was assessed. Two additional assessments were performed at 10-min intervals.

For assessment, each animal was placed on the bottom of a small upright box (11×7 0.5×4.5 cm). The walls of the box were made of translucent methacrylate except one of the lateral surfaces (7.5 cm wide) which was a 3-mm wire mesh. The position of the animal was scored for 2 minutes according to the following criteria: 0=four paws on the floor; 1=three paws on the floor; 2=two paws on the floor; 3=one paw on the floor; and 4=four paws holding the wire mesh. If an animal keeps several positions within the 2-min observation, the seconds elapsed in each position will be recorded. Finally, mean scoring was calculated. The cataleptic activity of the compounds by the oral route was simultaneously assessed in rats and expressed as effective dose 50% ($ED_{50}$). The results obtained are tabulated in Table 3 as inhibitory dose 50% ($ID_{50}$, mg/kg) in the climbing behaviour test and as $ED_{50}$ (mg/kg) in the catalepsy test. The therapeutic index (TI), which is a safety measurement for the use of test compounds, is also shown in Table 3.

TABLE 3

| Compound | Climbing $ID_{50}$ | Catalepsy $ED_{50}$ | TI = $ED_{50}/ID_{50}$ |
|---|---|---|---|
| Example 3 | 0.21 | 6.79 | 32.3 |
| Example 6 | 5.87 | >100 (*) | >17 (*) |
| Ex. 2' ES9600323 | 0.25 | 3.8 | 15.2 |
| Haloperidol | 0.32 | 2.00 | 6.25 |

(*) undetermined

According to the data of Table 3, the compounds of Examples 3 and 6 of the present invention have a higher therapeutic index than the compound of Example 2' of Spanish Patent Application No. 9600323 and than haloperidol, which confirms the advantage of a lower risk of extrapyramidal effects at the therapeutic doses.

The compounds of the present invention may be used as antipsychotic agents for the treatment of psychosis and schizophrenia by the oral, inyectable or rectal route at daily doses ranging from 1 to 500 mg, preferably between 2 and 50 mg inclusive. The usual oral administration forms as antipsychotic agents are solutions, tablets, coated-tablets, capsules, granules, syrups and the like. The compounds of the present invention may also be used as antihistamines for the treatment of allergy by the oral, injectable or rectal route at daily doses ranging from 1 and 500 mg, preferably between 2 and 150 mg inclusive. For the oral administration of these compounds in the treatment of allergy, solutions, tablets, coated-tablets, capsules, granules, syrups and the like may be administered. As antiallergic agents, they may also be administered in topical formulations, such as cream, ointment, lotion, powder and the like at concentrations ranging from 0.5 to 5%, preferably between 1 and 2% inclusive.

EXAMPLE 1

7-[3-[4-(6-fluorobenzo[d]isoxazole-3-yl)piperidine-1-yl]propoxy]-3-formyl-chromen-4-one To a solution of 2 mL (23 mmoles) of oxalyl chloride in 35 mL of dry dichloromethane, cooled at −70°C., was added drop by drop a solution of 3 mL (42 mmoles) of dimethyl sulfoxide dissolved in 10 mL of dichloromethane and the mixture was stirred for 5 minutes. Then 5 g (11 mmoles) of 7-[3-[4-(6-fluorobenzo[d]isoxazole-3-yl)piperidin-1-yl]propoxy]-3-(hydroxymethyl)-chromen-4-one (Patent ES 9600323) were added in several portions for 15 minutes and stirred for further 30 minutes at −70° C. 15 mL (107 moles) of triethylamine were added drop by drop and stirred overnight while allowed to warm to room temperature gradually. By cooling at −20° C., 50 mL of water were added, the mixture was allowed to warm to room temperature and the organic phase was decanted, dried over sodium sulphate and evaporated. The solid obtained was purified by chromatography on a silica gel column. Elution of the column with $CHCl_3:CH_3OH$ (98:2, v/v) gave 2.12 g of 7-[3-[4-(6-fluorobenzo[d]isoxazole-3-yl)piperidin-1-yl]propoxy]-3-formyl-chromen-4-one in 43% yield, mp 163–5° C.

IR (KBr): 1691, 1652, 1619, 1441 $cm^{-1}$.

NMR ($CDCl_3$): 2.10 (m, 6H), 2.20 (m, 2H), 2.60 (t, 2H), 3.10 (m, 3H), 4.19 (t, 2H), 6.96 (d, 1H), 7.05 (m, 2H), 7.24 (dd, 1H), 7.69 (dd, 1H), 8.19 (d, 1H), 8.47 (s, 1H), 10.37 (s, 1H).

EXAMPLE 2

7-[3-[4-(6-fluorobenzo[d]isoxazole-3-yl)piperidin-1-yl]propoxy]-4-oxochromene-3-carboxylic acid hydrochloride A mixture of 0.87 g (3 mmoles) of 7-(3-chloropropoxy)-4-oxochromene-3-carboxylic acid, 0.7 g (3 mmoles) of 6-fluoro-3-(4-piperidinyl)-benzo[d]isoxazole hydrochloride, 0.85 g (6 mmoles) of anhydrous potassium carbonate and a catalytic amount of potassium iodide in 25 mL of N,N-dimethylformamide was heated to 89–90° C. for 24 hours. After being cooled, the solution was poured onto 125 mL of water and then neutralized with HCl at pH 7. The precipitate obtained was filtered, washed with water and dried at vaccum. The solid was dissolved in 60 mL of 0.1M NaOH, diluted with water to 300 mL and the solution was washed with ethyl acetate. The aqueous solution was acidified with HCl to pH 1–2, and the precipitate obtained was filtered and dried at vaccum to give 0.62 g of 7-[3-[4-(6-fluorobenzo[d]isoxazole-3-yl)piperidin-1-yl]propoxy]-4-oxochromene-3-carboxylic acid hydrochloride in 40% yield.

IR(KBr): 3100–3700, 1698, 1616, 1447, 1384, 1165, 1121 cm$^{-1}$.

NMR (DMSO): 2.13 (m, 6H), 2.30 (m, 2H, piperidine $-2H_a$ and $-6H_a$), 2.67 (t, J=7.5 Hz, 2H, O—CH$_2$—CH$_2$—CH$_2$—N), 3.16 (d+m, 3H, piperidine $-2H_e$, $-4H$ and $-6H_e$), 4.10 (t, J=6Hz, 2H, O—CH$_2$), 6.67 (s, 1H, 8-H), 6.79 (d, J=8.7 Hz, 1H, 6-H), 7.10 (td, J=8.4 and 2.1 Hz, 1H, benzisoxazole-5H), 7.27 (dd, J=8.4 and 2.1 Hz, 1H, benzisoxazole-7H), 7.79 (dd, J=8.4 and 5.4 Hz, 1H, benzisoxazole-4H), 7.97 (d, J=8.7 Hz, 1H, -5H), 9.86 (s, 1H, 2-H).

EXAMPLE 3

7-[3-[4-(6-fluorobenzo[d]isoxazole-3-yl)piperidin-1-yl]propoxy]-3-methoxymethyl-chromen-4-one hydrochloride A solution of 2 g (4.4 mmoles) of 7-[3-[4-(6-fluorobenzo[d] isoxazole-3-yl)piperidin-1-yl]propoxy]-3-(hydroxymethyl)-chromen-4-one in 20 mL of 2M HCl in methanol was heated at reflux for 2 hours. The solvent was evaporated and the residue was dissolved in dichloromethane and washed with saturated CO$_3$HNa solution. The organic phase was evaporated, dissolved in acetonitrile and precipitated by addition of etheral HCl solution. The solid obtained was recrystallized from methanol to give 0.75 g of 7-(3-[4-(6-fluorobenzo[d] isoxazole-3-yl)piperidin-1-yl]propoxy]-3-methoxymethyl-chromen-4-one hydrochloride in 34% yield, mp 219–221° C.

IR(KBr): 1659, 1615, 1443, 1273, 1244 cm$^{-1}$.

NMR (CDC$_1$-CD$_3$OD): 2.25 (m, 2H), 2.50 (m, 2H), 2.90 (m, 2H), 3.05 (m, 2H), 3.35 (m, 2H), 3.48 (s, 3H), 3.60 (m, 1H), 3.80 (d, 2H), 4.20 (m, 2H), 4.39 (s, 2H), 6.90 (d, 1H), 6.97 (d, 1H), 7.16 (td, 1H), 7.66 (dd, 1H), 7.95 (s, 1H), 8.10 (d, 1H), 8.20 (dd, 1H).

EXAMPLE 4

7-hydroxy-2-(hydroxymethyl)-chromen-4-one

To a suspension of 5 g (21 mmoles) of ethyl 7-hydroxy-4-oxo-chromen-2-carboxylate and 5 g (45 mmoles) of anhydrous calcium chloride in 100 mL of absolute ethanol, cooled at 0° C., were added 3 g of sodium borohydride in several portions and the mixture was stirred at room temperature for 16 hours. Further 1 g of sodium borohydride was added and stirred for an additional 2 hours. The reaction mixture was suspended in 200 mL of water and acidified slowly with HCl. The precipitate was filtered, washed with water and dried at vaccum to give 2.7 g de 7-hydroxy-2-(hydroxymethyl)-chromen-4-one as a solid, yield 66%, mp 250–252° C.

IR(KBr): 2700–3500, 1650, 1634, 1570, 1458, 1326, 1250, 1101 cm$^{-1}$

NMR (d$_6$-DMSO): 3.50 (s, wide, 2H, OH), 4.40 (s, 2H, CH$_2$OH), 6.20 (s, 1H, 3-H), 6.82 (d, J=2.4 Hz, 1H, 8-H), 6.92 (dd, J=8.7 and 2.4 Hz, 1H, 6-H), 7.86 (d, J=8.7, 1H, 5-H).

EXAMPLE 5

7-(3-chloropropoxy)-2-(hydroxymethyl)-chromen-4-one

A mixture of 6 g (31 mmoles) of the compound obtained in Example 4, 6 mL (61 mmoles) of 1-bromo-3-chloropropane, 4.3 g (31 mmoles) of anhydrous potassium carbonate in 100 mL of acetone and 25 mL of N,N-dimethylformamide was heated at reflux for 16 hours. The reaction mixture was poured onto 100 mL of water and extracted with 100 mL of ethyl acetate. The organic extracts were washed with two portions of 100 mL of water, dried over sodium sulphate and evaporated at vaccum. The residue obtained was suspended in 25 mL of ethyl ether, filtered and dried at vaccum to give 4.2 g of 7-(3-chloropropoxy)-2-(hydroxymethyl)-chromen-4-one in 50% yield, mp 110–112° C.

IR(KBr): 2600–3500, 1651, 1628, 1592, 1448, 1246, 1099 cm$^{-1}$

NMR (CDCl$_3$): 2.28 (m, 2H, O—CH$_2$—CH$_2$), 3.76 (t, J=6 Hz, 2H, CH$_2$Cl), 4.16 (t, J=6 Hz, 2H, O—CH$_2$), 4.57 (s, 3H, CH$_2$OH+OH), 6.44 (s, 1H, 3-H), 6.78 (d, J=2,1 Hz, 1H, 8-H), 6.90 (dd, J=8,7 and 2.1 Hz, 1H, 6-H), 7.99 (d, J=8.7 Hz, 1H, 5-H).

EXAMPLE 6

7-[3-[4-(6-fluorobenzo[d]isoxazole-3-yl)piperidin-1-yl]propoxy]-2-(hydroxymethyl)-chromen-4-one hydrochloride A mixture of 3 g (11 mmoles) of the compound obtained in Example 5, 2.88 g (11 mmoles) of 6-fluoro-3-(4-piperidinyl)-benzo[d]isoxazole hydrochloride, 2.16 g (26 mmoles) of sodium bicarbonate and a catalytic amount of potassium iodide in 80 mL of acetonitrile was heated at reflux for 48 hours. The mixture was then allowed to cool, poured onto 100 mL of water and extracted with 100 mL of chloroform. The chloroform extract was washed with water, dried over sodium sulphate and evaporated. The residue obtained was suspended in ethyl ether, filtered and dried at vaccum to give 2 g of 7-[3-[4-(6-fluorobenzo[d]isoxazole-3-yl)piperidin-1-yl]propoxy]-2-(hydroxymethyl)-chromen-4-one in 40% yield.

NMR (CDCl$_3$): 2.0–2.2 (m, 8H), 2.60 (t, J=7.2 Hz, 2H, N—C$_2$—CH$_2$—CH$_2$—O), 3.10 (d+m, 3H, piperidine $-2H_e$, $-4H$ and $-6H_e$), 4.13 (t, J=6.6 Hz, 2H, O—CH$_2$—CH$_2$—CH$_2$), 4.58 (s, 3H, CH$_2$OH), 6.41 (s, 1H, 3-H), 6.89 (d, J=2,1 Hz, 1H, 8-H), 6.94 (dd, J=8.7 and 2.1 Hz, 1H, 6-H), 7.07 (td, J=8.7 and 2.4 Hz, 1H, benzisoxazole-5H), 7.25 (dd, J=8.7 and 2.4 Hz, 1H, benzisoxazole-7H), 7.71 (dd, J=8.7 and 5.1 Hz, 1H, benzisoxazole-4H), 8.04 (d, J=8.7 Hz, 1H, 5-H).

Hydrochloride: The product obtained was dissolved in a mixture of chloroform:methanol (3:1) and precipitated by addition of HCl methanol solution to give 1.4 g of 7-[3-[4-(6-fluorobenzo[d] isoxazole-3-yl)piperidin-1-yl]propoxy]-2-(hydroxymethyl)-chromen-4-one hydrochloride, as a solid, mp 248–251° C.

IR(KBr): 3300, 2500, 1648, 1603, 1439, 1329, 1122, 1094 cm$^{-1}$.

EXAMPLE 7

0.025% Injection Formulation
Composition for 1 ampoule
  compound of Example 3 . . . 0.5 mg
  methyl p-hydroxybenzoate . . . 1.0 mg
  propyl p-hydroxybenzoate . . . 0.1 mg
  bidistilled water q.s . . . 2.0 mL

EXAMPLE 8

0.1% oral solution formulation
Composition for 100 ml
  compound of Example 3 . . . 100 mg
  methyl p-hydroxybenzoate . . . 135 mg
  propyl p-hydroxybenzoate . . . 15 mg
  sorbitol 70% . . . 20 mg
  sodium saccharin . . . 50 mg
  orange essence . . . 0.25 mL
  distilled water q.s. . . . 100 mL

EXAMPLE 9

1 mg Tablet Formulation
Composition for 1 tablet
  compound of Example 3 . . . 1.0 mg
  corn starch . . . 32.4 mg
  talc . . . 4.5 mg
  hydrogenated castor oil . . . 1.5 mg
  lactose q.s . . . 150.0 mg

EXAMPLE 10

5 mg Tablet Formulation
Composition for 1 tablet
  compound of Example 3 . . . 5.0 mg
  corn starch . . . 43.2 mg
  talc . . . 6.0 mg
  hydrogenated castor oil . . . 2.0 mg
  lactose q.s. . . . 200.0 mg

EXAMPLE 11

10 mg Tablet Formulation
Composition for 1 tablet
  compound of Example 3 . . . 10.0 mg
  corn starch . . . 40.0 mg
  sodium lauryl sulphate . . . 0.50 mg
  pregelatinized corn starch . . . 8.00 mg
  magnesium stearate . . . 1.20 mg
  lactose q.s . . . 240.00 mg

EXAMPLE 12

1% Topical Cream Formulation
Composition for 100 g
  compound of Example 3 . . . 1.00 g
  isopropyl myristate . . . 9.00 g
  cetostearyl alcohol . . . 6.00 g
  propylene glycol . . . 3.00 g
  fatty acid polyglycolic ester . . . 5.00 g
  oleic acid decyl ester . . . 6.00 g
  perfume . . . 0.30 g
  methyl p-hydroxybenzoate . . . 0.15 g
  propyl p-hydroxybenzoate . . . 0.02 g
  ethyl p-hydroxybenzoate . . . 0.03 g
  demineralized water q.s . . . 100.00 g

What is claimed is:

1. 7-[3-[4-(6-fluorobenzo[d]isoxazol-3-yl)piperidin-1-yl]propoxy]-chromen-4-one derivatives of formula (I):

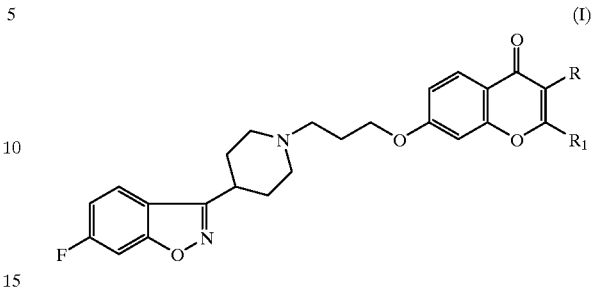

wherein R is hydrogen, CHO, $CH_2OR_2$ or COOH; $R_1$ is hydrogen or $CH_2OH$; and $R_2$ is alkyl having 1 to 4 carbon atoms with the proviso that one of substituents R and $R_1$ should be hydrogen, as well as their pharmaceutically acceptable salts.

2. The derivatives according to claim 1 of formula (I) wherein R is CHO, $CH_2OR_2$ or COOH and $R_1$ is hydrogen, or R is hydrogen and $R_1$ is $CH_2OH$.

3. The compounds of claim 1, as well as their pharmaceutically acceptable addition salts, for use in the treatment of psychosis, schizophrenia and allergy.

4. A pharmaceutically composition comprising a compound of formula (I) according to claim 1 or 2, or a pharmaceutically acceptable salt thereof, and a pharmaceutically acceptable carrier.

5. The use of a compound of claims 1 or 2 for preparing a pharmaceutical composition for the treatment of psychosis, schizophrenia and allergy.

6. A method of treatment of psychosis, schizophrenia and allergy which comprises administering to a mammal an effective amount of a compound of formula (I) according to claim 1 or 2, or a pharmaceutically acceptable addition salt thereof.

7. A process for preparing a compound of formula (I) according to claim 1 or 2, which comprises reacting the intermediates of the formula (II):

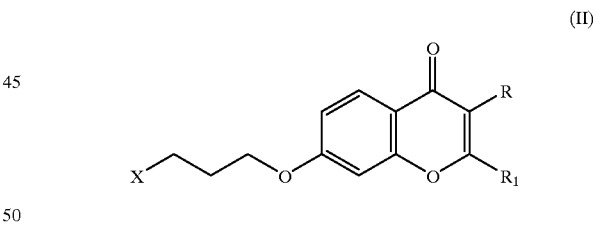

wherein R and $R_1$ is as defined for (I) and X is a halogen selected preferably between chlorine or bromine, with the intermediate of formula (III):

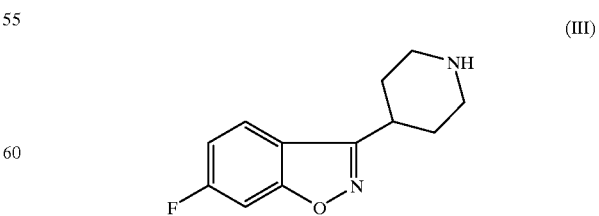

followed by optional reaction with the corresponding acid if their pharmaceutically acceptable salts are to be obtained.

* * * * *